(12) United States Patent
Barbero-Ortega et al.

(10) Patent No.: US 12,367,358 B2
(45) Date of Patent: Jul. 22, 2025

(54) ANTI-FOGGING BARCODE READER

(71) Applicants: Ventana Medical Systems, Inc., Tucson, AZ (US); Integrity Data Solutions, Inc., Tempe, AZ (US)

(72) Inventors: Isabel Barbero-Ortega, Seattle, WA (US); Ramon R. Salazar, Oro Valley, AZ (US); John M. Tavis, Queen Creek, AZ (US)

(73) Assignees: Ventana Medical Systems, Inc., Tucson, AZ (US); Integrity Data Solutions, Inc., Tempe, AZ (US)

( * ) Notice: Subject to any disclaimer, the term of this patent is extended or adjusted under 35 U.S.C. 154(b) by 0 days.

(21) Appl. No.: 18/514,532

(22) Filed: Nov. 20, 2023

(65) Prior Publication Data

US 2024/0086658 A1    Mar. 14, 2024

Related U.S. Application Data

(63) Continuation of application No. 16/926,160, filed on Jul. 10, 2020, now abandoned, which is a continuation of application No. PCT/EP2019/050502, filed on Jan. 10, 2019.

(60) Provisional application No. 62/616,367, filed on Jan. 11, 2018.

(51) Int. Cl.
*G06K 7/10* (2006.01)
*G01N 33/53* (2006.01)
*G01N 35/00* (2006.01)

(52) U.S. Cl.
CPC .......... *G06K 7/10821* (2013.01); *G01N 33/53* (2013.01); *G01N 35/00029* (2013.01); *G01N 2035/00138* (2013.01)

(58) Field of Classification Search
CPC .......... G06K 7/10821; G06K 7/10693; G06K 7/10722; G06K 7/1478; G06K 7/14; G01N 35/00029; G01N 33/53; G01N 35/00732
USPC ............. 235/462.01, 462.11, 462.41, 462.24
See application file for complete search history.

(56) References Cited

U.S. PATENT DOCUMENTS

| | | | |
|---|---|---|---|
| 2005/0186114 A1 | 8/2005 | Reinhardt et al. | |
| 2006/0011305 A1* | 1/2006 | Sandell | B01L 3/5027 156/499 |
| 2006/0226228 A1 | 10/2006 | Gagne et al. | |
| 2007/0002442 A1* | 1/2007 | Choi | H04N 1/00 359/507 |

(Continued)

FOREIGN PATENT DOCUMENTS

| | | | | |
|---|---|---|---|---|
| CA | 2730903 A1 * | 1/2010 | ............. | G03B 11/00 |
| FR | 2904508 A1 * | 2/2008 | ............. | B32B 17/06 |

*Primary Examiner* — Edwyn Labaze
(74) *Attorney, Agent, or Firm* — Charney IP Law LLC; Thomas M. Finetti

(57) ABSTRACT

An automated specimen processing system is provided for performing slide processing operations on slides bearing biological samples. In some embodiments, the disclosed specimen processing system includes a barcode reader having a heated window. In some embodiments, the barcode reader having the heated window is configured to read information stored within a label affixed to a slide, whereby the barcode reader may be operated within a hot and/or humid environment. A method for automated processing of slides also is provided, whereby the method utilizes the information retrieved from a label affixed to determine which one or more slide processing operations to perform.

22 Claims, 12 Drawing Sheets

(56) References Cited

U.S. PATENT DOCUMENTS

| | | | |
|---|---|---|---|
| 2007/0152065 A1* | 7/2007 | Gong | G06K 7/10702 235/462.43 |
| 2009/0068062 A1* | 3/2009 | Jafari | G01N 1/38 436/179 |
| 2011/0115972 A1 | 5/2011 | Voges | |

* cited by examiner

ANTI-FOGGING BARCODE READER

CROSS-REFERENCE TO RELATED APPLICATIONS

This application is a continuation of U.S. patent application Ser. No. 16/926,160 filed on Jul. 10, 2020, which application is a continuation of PCT/EP2019/050502 filed on Jan. 10, 2019, which application claims priority to and the benefit of U.S. provisional patent application No. 62/616,367, the disclosures of which are hereby incorporated by reference herein in their entireties.

BACKGROUND OF THE DISCLOSURE

Immunohistochemical (IHC) slide staining can be utilized to identify proteins in cells of a tissue section and hence is widely used in the study of different types of cells, such as cancerous cells and immune cells in biological tissue. Thus, IHC staining may be used in research to understand the distribution and localization of the differentially expressed biomarkers of immune cells (such as T-cells or B-cells) in a cancerous tissue for an immune response study. For example, tumors often contain infiltrates of immune cells, which may prevent the development of tumors or favor the outgrowth of tumors.

In-situ hybridization (ISH) can be used to look for the presence of a genetic abnormality or condition such as amplification of cancer-causing genes specifically in cells that, when viewed under a microscope, morphologically appear to be malignant. In situ hybridization (ISH) employs labeled DNA or RNA probe molecules that are anti-sense to a target gene sequence or transcript to detect or localize targeted nucleic acid target genes within a cell or biological sample. ISH is performed by exposing a cell or tissue sample immobilized on a glass slide to a labeled nucleic acid probe which is capable of specifically hybridizing to a given target gene in the cell or tissue sample. Several target genes can be simultaneously analyzed by exposing a cell or tissue sample to a plurality of nucleic acid probes that have been labeled with a plurality of different nucleic acid tags. By utilizing labels having different emission wavelengths, simultaneous multicolored analysis may be performed in a single step on a single target cell or tissue sample.

Primary staining, special staining, immunochemical analyses, and in situ hybridization analyses are utilized to analyze a variety of biological samples including microarray samples, biological samples and tissue array samples. These techniques are inherently inconsistent when performed manually, especially by multiple different persons. Inconsistent staining makes it difficult for a pathologist or other medical or research personnel to interpret samples and to make comparisons between different samples. Thus, a number of devices and methods have been described that serve to automate the staining process and reduce staining inconsistency.

BRIEF SUMMARY OF THE DISCLOSURE

Automated specimen processing systems often include steps whereby fluids are dispensed and/or removed from a sample, sometimes repeatedly. In some embodiments, heaters are used to evaporate certain fluids dispensed to a sample. In some embodiments, the collection of heat and humidity within a specimen processing system results in fogging and/or the build-up of condensate on components within the specimen processing system. In some embodiments, fogging of a barcode reader disposed within the specimen processing system causes the barcode reader to operate erroneously (e.g. incorrectly read a barcode) or not work at all (see, e.g., FIG. 6A). The present disclosure provides for a sealed (e.g. air tight) barcode reader having a window which resists or mitigates fogging and/or the build-up of condensate (see, e.g. FIG. 6B).

In one aspect of the present disclosure is a barcode reader comprising: (a) a sealed housing including an optically transparent window, wherein the optically transparent window comprises a substrate and an electroconductive layer disposed on a surface of the substrate; (b) a pair of conductors in communication with the electroconductive layer; and (c) a power source in communication with the pair of conductors. In some embodiments, the sealed housing including the optically transparent window is air-tight. In some embodiments, the substrate is comprised of glass or plastic. In some embodiments, the electroconductive layer comprises a metal oxide or a dropped metal oxide. In some embodiments, the metal oxide is a tin oxide. In some embodiments the metal oxide is indium tin oxide. In some embodiments, the metal oxide is a zinc oxide. In some embodiments the electroconductive layer comprises a thickness ranging from between about 5 nm to about 10,000 nm. In some embodiments, the pair of conductors are first and second electrical contacts, such as metal contacts, which directly contact but are not adhered to the electroconductive layer. In some embodiments, the pair of conductors are first and second bus bars, such as bus bars deposited onto the electroconductive layer. In some embodiments, the power source supplies between about 1V to about 10V to the electroconductive layer. In some embodiments, the barcode reader further comprises a camera and a controller. In some embodiments, a temperature of the optically transparent window ranges from between 30° C. and 60° C. In some embodiments, a temperature of the optically transparent window ranges from between 35° C. and 50° C.

In another aspect of the present disclosure is an automated specimen processing system, comprising: (a) a slide holder within the automated specimen processing system, wherein the slide holder bears slides having (i) a biological specimen disposed thereon, and (ii) and identifying indicia; (b) at least one barcode reader having a sealed housing including a heated window, the heated window comprising an electroconductive layer disposed on a surface of the substrate and wherein the barcode reader is configured to read information from the identifying indicia; and (c) a dispenser within the automated specimen processing system configured to independently deliver a plurality of fluids (e.g. wash fluids, buffers, etc.) or reagents (e.g. hematoxylin, antibodies, nucleic acid probes, etc.) to each individual slide within the slide holder based on the identifying indicia present on the individual slide. In some embodiments, the automated specimen processing system further comprises a control module in electrical communication with the at least one barcode reader. In some embodiments, the control module is configured to receive information from the at least one barcode reader and command a dispenser to dispense the plurality of fluids or reagents based on the information received from the at least one barcode reader. In some embodiments, an atmosphere within the sealed housing of the barcode reader is different than an atmosphere outside the sealed housing. In some embodiments, the electroconductive layer is in communication with a power source. In some embodiments, the power source supplies between about 1V and about 10V to the electroconductive layer. In some embodiments, a temperature of the heated window ranges from between 30°

C. and 60° C. In some embodiments, a temperature of the heated window ranges from between 35° C. and 50° C. In some embodiments, the electroconductive layer is comprised of indium tin oxide.

In another aspect of the present disclosure is an apparatus for automatically treating biological specimens, comprising: at least one slide tray holding a plurality of slides, such as for holding slides in substantially horizontal positions, wherein said biological specimens are located on the slides; at least one barcode reader comprising a sealed housing having a heated window, the heated window in communication with a power source; one or more workstations that receive the slide tray and perform one or more slide processing operations on the plurality of slides held in the slide tray; and a transporter that moves the slide tray into and out of the one or more workstations. In some embodiments, the apparatus further includes a fluidics module in fluid communication with the one or more workstations that supplies a reagent to the one or more workstations. In some embodiments, the apparatus further includes a pneumatics module in fluid communication with the one or more workstations and the fluidics module; wherein the pneumatics module supplies vacuum and/or pressurized gas to the one or more workstations and the fluidics module. In some embodiments, the apparatus further includes a control module in electrical communication with the at least one barcode reader, the transporter, the one or more workstations, the fluidics module and said pneumatics module, wherein the control module coordinates function of components of the apparatus during treatment of the biological specimens based on information received from the at least one barcode reader.

In some embodiments, the at least one of the one or more workstations that receive the slide tray and perform the one or more slide processing operation comprises a moveable nozzle assembly, wherein the nozzle assembly includes one or more nozzles through which a reagent is delivered to a slide. In some embodiments, the power source supplies between about 1V and about 10V to the electroconductive layer. In some embodiments, a temperature of the heated window ranges from between 30° C. and 60° C. In some embodiments, a temperature of the heated window ranges from between 35° C. and 50° C. In some embodiments, the electroconductive layer is comprised of indium tin oxide.

In another aspect of the present disclosure is an automated method for processing a plurality of slides bearing biological tissue samples, comprising: reading information stored on a label of each of the plurality of slides using a barcode reader, wherein the barcode reader comprises a sealed housing having a heated window, the heated window comprising at least one electroconductive layer in communication with a power source; performing a set of slide processing operations on each individual slide of the plurality of slides in one or more workstations, wherein the slide processing operations for each individual slide of the plurality of slides is determined based on the information read from the label of each individual slide. In some embodiments, the set of slide processing operations performed on each individual slide includes at least staining samples on the slides by flowing one or more stains from at least one reagent container, through a fluidics module, and out at least one dispense nozzle positioned above the slide tray. In some embodiments, the method further comprises transporting the slide tray holding the plurality of slides to an automated coverslipper workstation after performing the set of slide processing operations that include at least staining and solvent-exchange. In some embodiments, the method further comprises performing a solvent-exchange.

In some embodiments, the method further comprises coverslipping the plurality of slides held in the slide tray with separate respective coverslips using the automated coverslipper workstation. In some embodiments, the set of slide processing operations further includes heating the plurality of slides sufficiently to adhere the biological samples to the slides. In some embodiments, the set of slide processing operations further includes de-paraffinizing. In some embodiments, the power source supplies between about 1V and about 10V to the electroconductive layer. In some embodiments, a temperature of the heated window ranges from between 30° C. and 60° C. In some embodiments, a temperature of the heated window ranges from between 35° C. and 50° C. In some embodiments, the electroconductive layer is comprised of indium tin oxide.

In another aspect of the present disclosure is an automated method for processing a plurality of slides bearing biological tissue samples, comprising: reading information stored on a label of each of the plurality of slides using a barcode reader, wherein the barcode reader comprises a sealed housing having a heated window, the heated window comprising at least one electroconductive layer in communication with a power source; performing a set of slide processing operations on the plurality of slides in one or more workstations, wherein the slide processing operations for each individual slide of the plurality of slides is determined based on the information read from the label of each individual slide, wherein the set of slide processing operations includes at least staining and solvent-exchanging, wherein the staining comprises treating the slides with a hematoxylin solution and an eosin solution by flowing the hematoxylin solution and the eosin solution from one or more reagent containers to at least one dispense nozzle via a fluidics module; and transporting the slide tray holding the plurality of slides to an automated coverslipper workstation. In some embodiments, the method may further comprise the step of dispensing one or more additional reagents, e.g. dispensing one or more antibodies or nucleic acid probes to the sample.

In some embodiments, the method further comprises coverslipping the plurality of slides held in the slide tray with separate respective coverslips using the automated coverslipper workstation. In some embodiments, the power source supplies between about 1V and about 10V to the electroconductive layer. In some embodiments, a temperature of the heated window ranges from between 30° C. and 60° C. In some embodiments, a temperature of the heated window ranges from between 35° C. and 50° C. In some embodiments, the electroconductive layer is comprised of indium tin oxide.

In another aspect of the present disclosure is an assembly comprising: (i) a barcode reader having a heated window; and (ii) a dispenser configured to introduce one or more fluids or reagents to a substrate, such as a substrate including a biological specimen and a label to be read by the barcode reader. In some embodiments, the assembly further comprises a control system. In some embodiments, the control system is configured to power the barcode reader having the heated window. In some embodiments, the control system if configured to relay signals to the assembly, such that the dispenser may introduce the appropriate fluids and/or regents in the appropriate amounts, such as based on information included within the label affixed to the slide. In some embodiments, the barcode reader and/or the dispenser are adapted to be moved relative to a substrate. In other embodiments, the substrate is provided within a holder which is movable relative to the barcode reader and/or the dispenser. In some embodiments, the control system supplies between about 1V and about 10V to the barcode reader such that the heated window is heated to a pre-determined temperature. In some embodiments, a temperature of the heated window ranges from between 30° C. and 60° C. In some embodiments, a temperature of the heated window ranges from between 35° C. and 50° C. In some embodiments, the heated window comprises an electroconductive layer is comprised of indium tin oxide or doped indium tin oxide. In some embodiments, a pair of electrical conductors are in communication with the heated window. In some embodiments, the pair of electrical conductors are selected from electrical contacts or bus bars. In some embodiments, the pair of electrical conductors are in communication with the control system. In some embodiments, the biological specimen is a tumor sample, whereby the tumor sample is contacted with at least one stain to label one or more biomarkers within the tumor sample.

In another aspect of the present disclosure is an assembly comprising: (i) a barcode reader having a heated window; and (ii) a transport apparatus to move a substrate to a position near the barcode reader, such that the barcode reader may read a label affixed to the substrate. In some embodiments, the barcode reader comprises an air-tight housing, where the heated window forms part of the air-tight housing. In some embodiments, the heated window is heated to a temperature ranging from between 35° C. and 50° C. In another aspect of the present disclosure is an assembly comprising: (i) a barcode reader having a heated window; and (ii) a transport apparatus to move the barcode reader to a position near a specimen-bearing substrate, such that the barcode reader may read a label affixed to the specimen-bearing substrate. In some embodiments, the barcode reader comprises an air-tight housing, where the heated window forms part of the air-tight housing. In some embodiments, the heated window is heated to a temperature ranging from between 35° C. and 50° C.

BRIEF DESCRIPTION OF THE FIGURES

For a general understanding of the features of the disclosure, reference is made to the drawings. In the drawings, like reference numerals have been used throughout to identify identical elements.

DETAILED DESCRIPTION

Figure 1A:
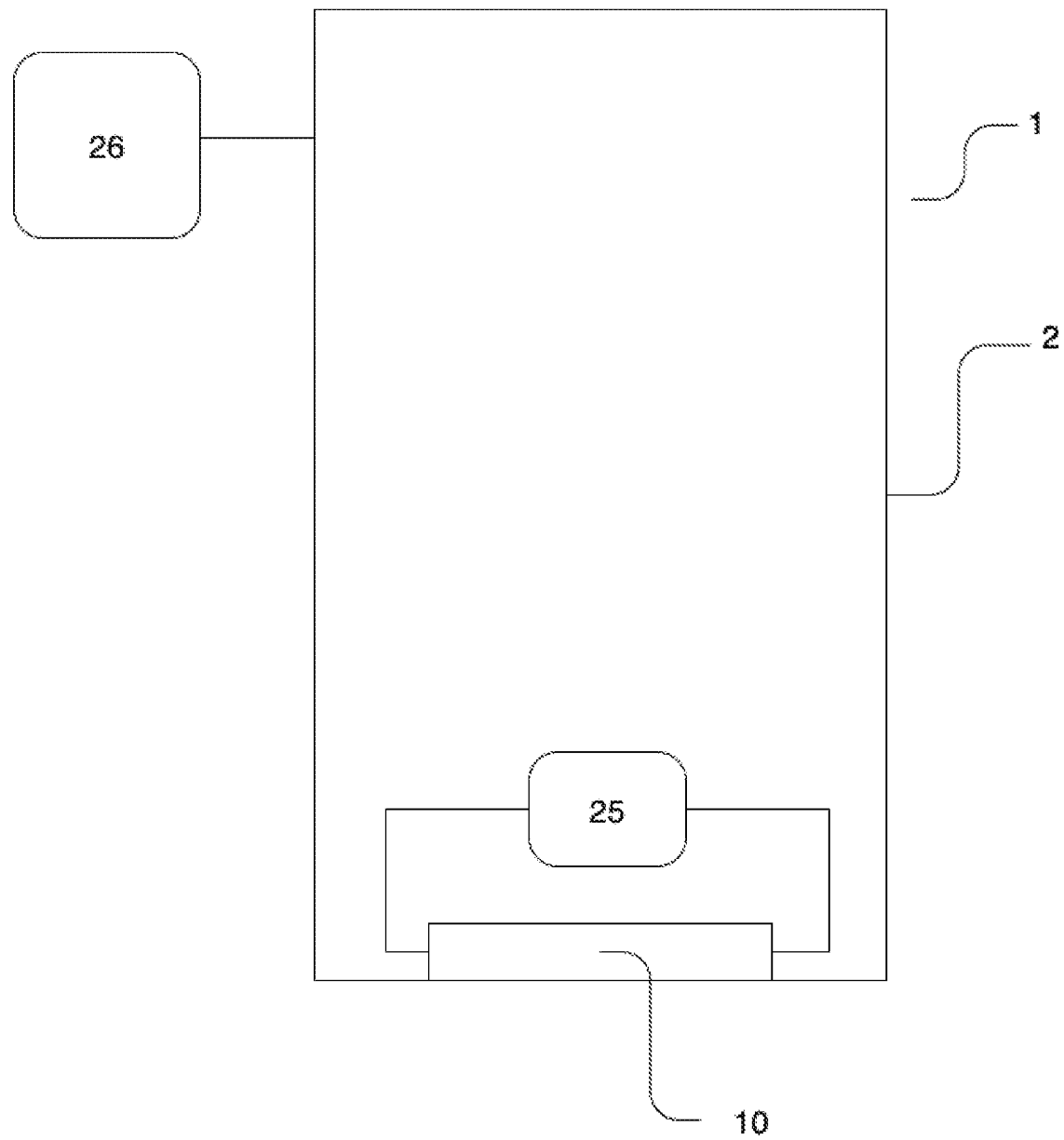
FIG. 1A provides a cross-section of a barcode reader having a heated window in accordance with some embodiments of the present disclosure.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c.

Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "biological sample," "tissue sample," "specimen" or the like refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "fluid" refers to any liquid, including water, solvents, solutions (e.g. buffer solutions), etc. The term "fluids" also refers to any mixtures, colloids, suspensions, etc. The term "fluids" also encompasses reagents, stains, and other specimen processing agents (e.g. glues, fixatives, etc.) which may be applied to a microscope slide and/or specimen. The fluids may be aqueous or non-aqueous. Further examples include solutions or suspensions of antibodies, solutions or suspensions of nucleic acid probes, and solutions or suspensions of dye or stain molecules (e.g., H&E staining solutions, Pap staining solutions, etc.). Still further examples of fluids include solvents and/or solutions for deparaffinizing paraffin-embedded biological specimens, aqueous detergent solutions, and hydrocarbons (e.g., alkanes, isoalkanes and aromatic compounds such as xylene). Still further examples of fluids include solvents (and mixtures thereof) used to dehydrate or rehydrate biological specimens.

As used herein, the term "reagent" refers to any liquid or liquid composition used in a slide processing operation that involves adding a liquid or liquid composition to a slide. Reagents include solutions, emulsions, suspensions and solvents (either pure or mixtures thereof). Reagents can be aqueous or non-aqueous. Examples of reagents include solutions or suspensions of antibodies, solutions or suspensions of nucleic acid probes, and solutions or suspensions of dye or stain molecules (such as H&E staining solutions and Pap staining solutions). Further examples of reagents include solvents and/or solutions for de-paraffinization of paraffin-embedded biological samples such as limonene, aqueous detergent solutions, and hydrocarbons (for example, alkanes, isoalkanes and aromatic compounds such as xylene). Additional examples of reagents include solvents (and mixtures thereof) that can be used to dehydrate or rehydrate biological samples, such as ethanol, water and mixtures thereof.

As used herein, the term "slide" refers to any substrate (e.g., substrates made, in whole or in part, glass, quartz, plastic, silicon, etc.) of any suitable dimensions on which a biological specimen is placed for analysis, and more particularly to a "microscope slide" such as a standard 3 inch by 1 inch microscope slide or a standard 75 mm by 25 mm microscope slide. Examples of biological specimens that can be placed on a slide include, without limitation, a cytological smear, a thin tissue section (such as from a biopsy), and an array of biological specimens, for example a tissue array, a cellular array, a DNA array, an RNA array, a protein array, or any combination thereof. Thus, in one embodiment, tissue sections, DNA samples, RNA samples, and/or proteins are placed on a slide at particular locations. In some embodiments, the term slide may refer to SELDI and MALDI chips, and silicon wafers.

As used herein, the terms "stain," "staining," or the like as used herein generally refers to any treatment of a biological specimen that detects and/or differentiates the presence, location, and/or amount (such as concentration) of a particular molecule (such as a lipid, protein or nucleic acid) or particular structure (such as a normal or malignant cell, cytosol, nucleus, Golgi apparatus, or cytoskeleton) in the biological specimen. For example, staining can provide contrast between a particular molecule or a particular cellular structure and surrounding portions of a biological specimen, and the intensity of the staining can provide a measure of the amount of a particular molecule in the specimen. Staining can be used to aid in the viewing of molecules, cellular structures and organisms not only with bright-field microscopes, but also with other viewing tools, such as phase contrast microscopes, electron microscopes, and fluorescence microscopes. Some staining performed by the system can be used to visualize an outline of a cell. Other staining performed by the system may rely on certain cell components (such as molecules or structures) being stained without or with relatively little staining other cell components. Examples of types of staining methods performed by the system include, without limitation, histochemical methods, immunohistochemical methods, and other methods based on reactions between molecules (including non-covalent binding interactions), such as hybridization reactions between nucleic acid molecules. Particular staining methods include, but are not limited to, primary staining methods (e.g., H&E staining, Pap staining, etc.), enzyme-linked immunohistochemical methods, and in situ RNA and DNA hybridization methods, such as fluorescence in situ hybridization (FISH).

The term "workstation" refers to a position or location in a disclosed system where at least one slide processing operation is performed, and more particularly to a modular unit inside of which one or more slide processing operations are performed on a plurality of slides held in a slide tray (for example, a plurality of slides held in a substantially horizontal position in a slide tray). A workstation can receive a slide tray in substantially a single position so that moveable components of the workstation can locate individual slides within the slide tray and precisely perform a slide processing operation on one or more slides in the tray (such as deliver a fluid, solution, reagent, etc. to a particular slide or portion thereof). Examples of slide processing operations that can be performed by a workstation include heating, drying, deparaffinizing, pre-stain prepping, rinsing, solvent exchanging, staining and coverslipping, and combinations thereof. In some embodiments, a workstation dispenses two or more fluids, solutions, reagents, etc. to a slide without the slides being moved from one workstation to another during a slide-processing operation or operations such as de-paraffinizing, staining and/or solvent exchanging. Thus, in one embodiment, a workstation includes a delivery means such as a nozzle or a manifold of nozzles through which fluids, solutions, reagents, etc. are delivered to slides held in a slide tray, which delivery means can be moveable or fixed in position within the workstation. Thus, in some embodiments, a workstation encompasses an active, mechanical device that delivers fluids (such as two or more fluids) to groups of slides held together in a slide tray. Thus, in one non-limiting aspect a work station is not a reagent bath in which slide are immersed. In other embodiments, a workstation can include a heating element and can further include a heat directing element. A heat directing element can help to spread heat more evenly between slides held in a slide tray. A workstation also can include one or more radiant heaters. A workstation also can include a tray tilter (such as a tilt pan) to lift one end of a slide tray to assist with liquid removal from the tray. Alternatively, a workstation can include a mechanism to tilt one or more individual slides in a slide tray away from a horizontal position. Workstations can further include various components that move or control other workstation components, such as stepper motors, screw drives and microprocessors. Other components that can be included in a workstation include hoses, belts, tracks, fluidics connections, metering pumps, metering valves, electrical connections, sensors and the like. In another embodiment, a workstation is a modular unit that can be interchanged between two or more positions within a disclosed system and electrically and fluidically connected to the system via a common electronics backplane and a common fluidics manifold. In yet another embodiment, a workstation can include a light source, such as a UV light source for curing an adhesive for holding a coverslip in place on a slide.

Overview

The build-up of condensate or fogging within the optical pathway of a barcode reader could negatively affect a barcode reader's ability to effectively "read" a barcode or other indicia present on a substrate, e.g. a label present on the microscope slide. The present disclosure provides barcode readers adapted to prevent or reduce fogging and/or the build-up of condensate within an optical pathway of the barcode reader when it is used in high heat and high humidity environments, such as the high heat and high humidity environments often found in automated specimen processing systems.

In some embodiments, the barcode readers of the present disclosure are adapted to read barcodes and/or other indicia present on a specimen-bearing substrate, e.g. a microscope slide. In these embodiments, the barcode may comprise information including patient information, diagnostic information, information pertaining to the type of biological sample or other tissue characteristics, and/or information about an assay to be run. This information must be read accurately such that a specimen processing system (e.g. a staining apparatus) may (i) apply the appropriate fluids and/or reagents to a biological sample, and/or (ii) perform the appropriate processing steps (and perform them in the correct order).

In some embodiments, a specimen processing system 5 of the present disclosure is capable of performing all or some of the steps of processing, staining, and coverslipping of biological samples mounted on a microscope slide. In some embodiments, slides bearing one or more biological samples and having a barcode disposed on one end of the slide are placed on or within a slide holder. A barcode reader 1 having a heated window positioned within the specimen processing system 5 may then be used to read a barcode disposed on the microscope slide. In some embodiments, the information retrieved from the barcode is supplied to a system controller 6 whereby it is interpreted and used by the specimen processing system 5 to processes the biological sample accordingly. For example, the slides may be individually processed through a sequence of steps in which the slides are baked, de-waxed, stained and finally coverslipped, based on the identification of a type of sample or type of assay to be run, where such information is included within the barcode affixed to the slide.

Barcode Reader

Figure 1B:
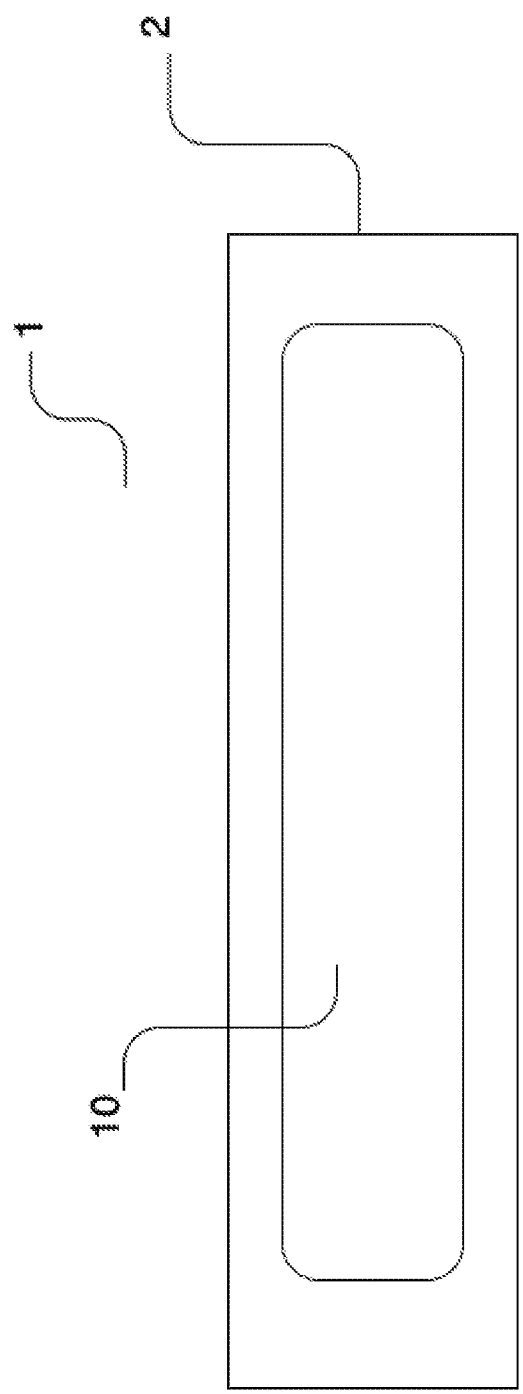
FIG. 1B illustrates a front view of a barcode reader having a heated window in accordance with some embodiments of the present disclosure.
Figure 1C:
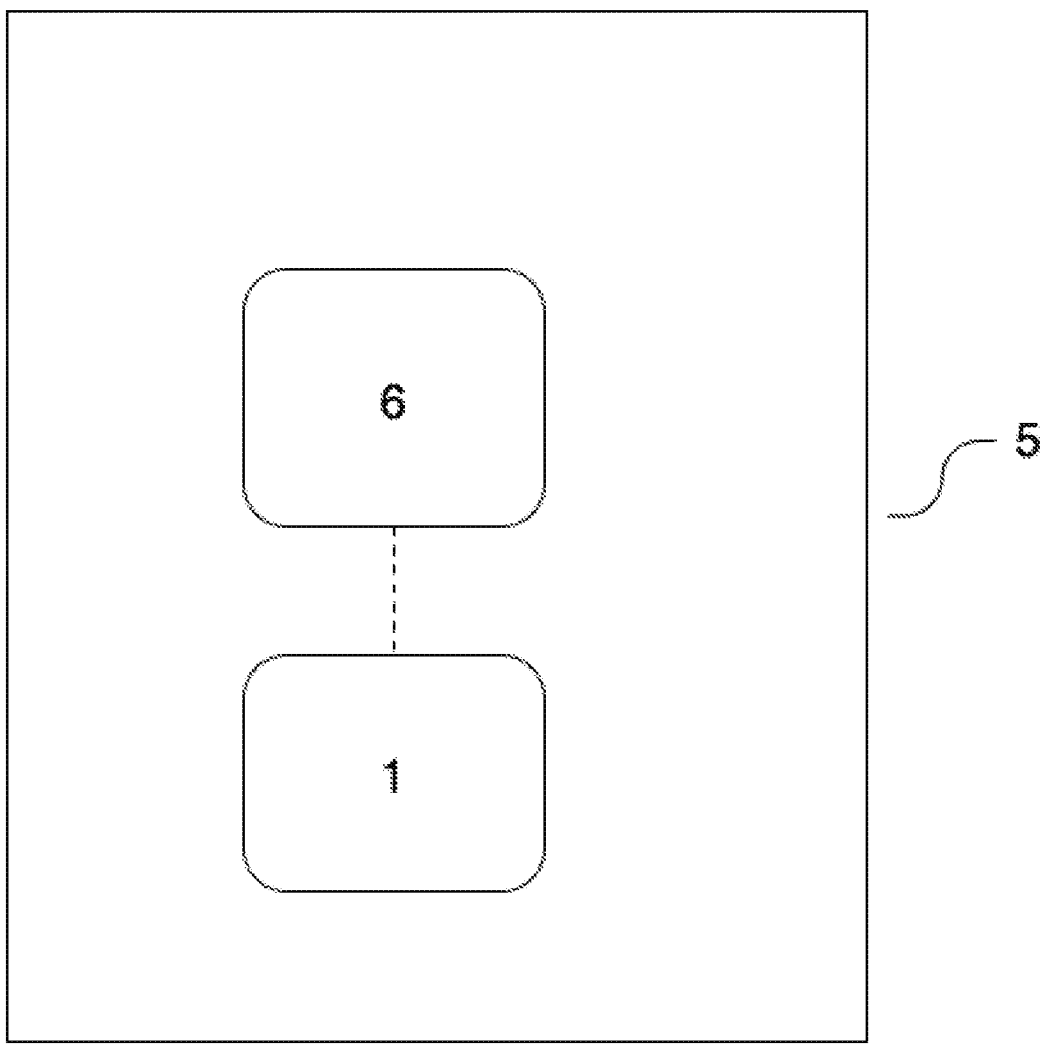
FIG. 1C illustrates a system, e.g. a specimen processing system, including a barcode reader having a heated window in accordance with some embodiments of the present disclosure.

As described in further detail herein, the present disclosure provides a barcode reader including a heated window. FIGS. 1A and 1B illustrate a barcode reader 1 including a housing 2. In some embodiments, the housing 2 is a sealed housing, e.g. an air tight housing. In some embodiments, the housing 2 prevents water vapor or other condensates from entering into the barcode reader 1. In some embodiments, the housing 2 is comprised of a metal or a plastic material.

As illustrated in FIGS. 1A and 1B, the housing 2 includes a heated window 10, whereby the housing 2 and the heated window 10 together form an air tight seal, a moisture-resistant seal, and/or a waterproof seal. In some embodiments, the heated window 10 is substantially optically transparent. In some embodiments, the heated window 10 is integral within the housing 2. In some embodiments, the heated window 10 is flush with the housing 2, e.g. the heated window is flush with the materials forming the walls of the housing 2. In other embodiments, the heated window 10 is adhered to or fixed to an internal surface of the housing 2 such that the heated window 10 is recessed within the housing 2. In yet other embodiments, the heated window 10 is mounted on an external surface of the housing 2. In some embodiments, the size of the heated window 10 may range from 0.5 cm by 1 cm to 1 cm by 10 cm. In other embodiments, the size of the heated window 10 may range from 0.5 cm by 1 cm to 1 cm by 8 cm.

In some embodiments, barcode reader 1 may be communicatively coupled to a controller 26, which may independently control operation of the heated window 10 and other components enclosed within the sealed housing 2 of the barcode reader 1. While controller 26 is depicted external to the housing 2, the controller 26 may be enclosed within the interior of the barcode reader 1. In some embodiments, the barcode reader 1 is may be further communicatively coupled to other system components, such as a computer system, the system controller 6, or other control logic which is part of the barcode reader or a specimen processing system.

In some embodiments, the controller 26 includes one or more sensors, such as a temperature sensor and/or a humidity sensor. In some embodiments, the sensors are located inside the sealed housing of the barcode reader 1, e.g. a first sensor positioned inside the sealed housing and a second sensor posited out the sealed housing. In other embodiments, at least one sensor is located outside the sealed housing of the barcode reader 1. In some embodiments, the controller 26 may utilize temperature and/or humidity measurements, such as temperature and/or humidity measurements external to the housing 2 and within the specimen processing system 5, so as to determine whether or not to supply power to the heated window 10. In some embodiments, the temperature measurements are utilized to maintain the heated window 10 at a temperature above a temperature within the specimen processing system, e.g. if a temperature outside the barcode reader 1 is 30° C., then the sufficient power is provided to the heated window 10 such that the heated window is heated to a temperature greater than 30° C., such as 35° C. In yet other embodiments, the one or more sensors are used to vary the power supplied to the heated window 10 such that the heated window can be variably heated, e.g. the power supplied to the heated window 10 may be increased after the heat and/or humidity within the specimen processing system 5 reaches a threshold amount. In some embodiments, temperature and/or humidity measurements are made by the specimen processing system 5 (not the barcode reader) and such information is transmitted from the system controller 6 to the barcode controller 26 such that an appropriate amount of power is supplied to the heated window 10. In some embodiments, the heated window 10 always receives power and thus is continuously heated. In some embodiments, the heated window 10 is heated only when heaters within the specimen processing apparatus are in active use.

Figure 2A:
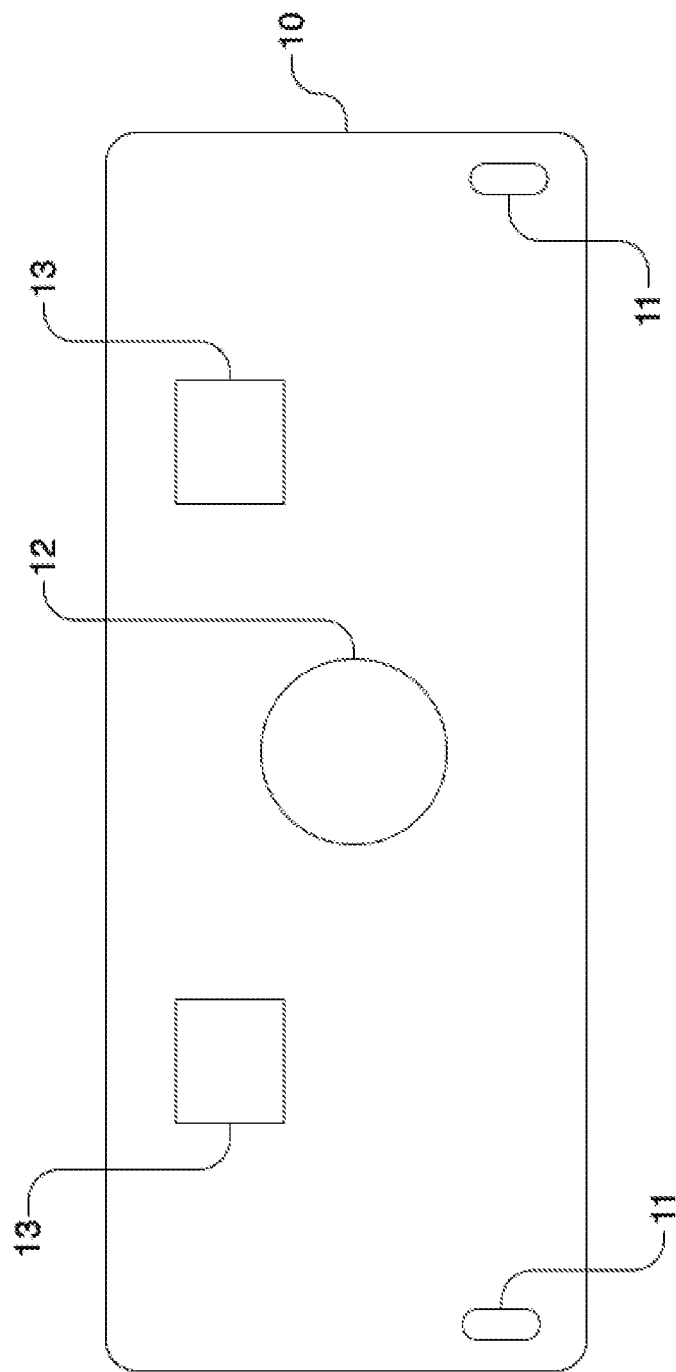
FIG. 2A illustrates a heated window of a barcode reader including two electrical contacts in communication with an electroconductive coating of the heated window in accordance with some embodiments of the present disclosure.
Figure 2B:
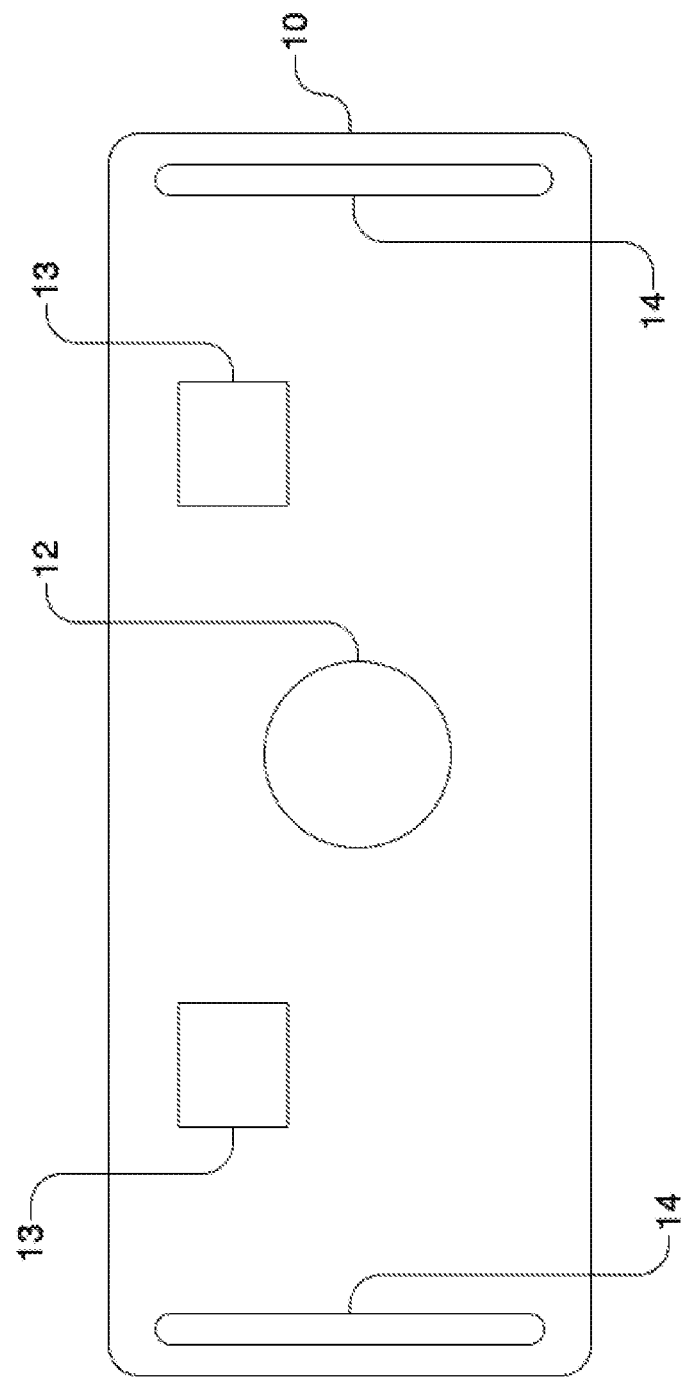
FIG. 2B illustrates a heated window of a barcode reader including two bus bars in communication with an electroconductive coating of the heated window in accordance with some embodiments of the present disclosure.

FIGS. 2A and 2B illustrate a heated window 10 of a barcode reader 1 in relation to other barcode reader 1 components. For example, positioned behind the heated window 10 (and internally within the barcode reader's 1 sealed interior) is a lens 12 configured to read a barcode or other graphical and/or optical indicia. In some embodiments, the barcode reader 1 is configured to read barcode symbols, including linear, two dimensional, and matrix barcodes. In some embodiments, the barcode reader 1 is configured to read other optical indicia including PDF417, MicroPDF417, MaxiCode, Data Matrix, QR Code, Aztec, Aztec Mesas, Code 49, EAN-UCC Composite, Snowflake, Dataglyphs, Code 39, Code 128, Codabar, UPC, EAN, Interleaved 2 of 5, Reduced Space Symbology, Code 93, Codablock F, and BC412, Planet Code, OCR-A, and OCR-B.

In some embodiments, one or more light sources 13 (e.g. LED lights, incandescent lights, halogen lights, etc.) are also positioned behind the heated window 10 (and, again, internally within the barcode reader's 1 sealed interior), the one or more light sources 13 configured to illuminate a target object, e.g. a barcode affixed to a microscope slide. In some embodiments, a set of electrical contacts 11 (FIG. 2A) or bus bars 14 (FIG. 2B) (collectively the electrical contacts or bus bars are referred to herein as "electrical conductors" or "conductors") are communicatively coupled with the heated window 10. In some embodiments, the electrical contacts 11 or bus bars 14 provide power to the an electroconductive coating or film of the heated window 10. Yet other components of barcode readers that may be incorporated into barcode reader 1 are disclosed in U.S. Pat. No. 9,286,502, the disclosure of which is hereby incorporated by reference herein in its entirety.

It is believed that the electroconductive coating or film of the heated window 10 is not a perfect conductor, and typically possesses an electrical resistance in a range of about 0.5 ohms per square to about 500 ohms per square. In some embodiments, the electrical resistance ranges from between about 2 ohms per square to about 350 ohms per square. In other embodiments, the electrical resistance ranges from between about 2 ohms per square to about 250 ohms per square. In yet other embodiments, the electrical resistance ranges from between about 5 ohms per square to about 150 ohms per square. In further embodiments, the electrical resistance ranges from between about 5 ohms per square to about 75 ohms per square. In yet further embodiments, the electrical resistance ranges from between about 50 ohms per square to about 250 ohms per square. In even further embodiments, the electrical resistance ranges from between about 75 ohms per square to about 200 ohms per square. Thus, an electric current flowing in the electroconductive coating or film will result in the formation of heat in proportion to the resistance of the film and the square of the current flowing in the electroconductive coating or film.

Figure 3:
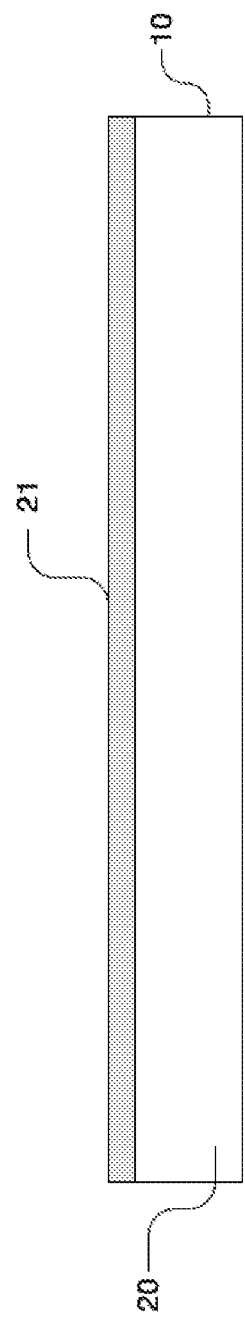
FIG. 3 illustrates an electroconductive material adhered to or deposited onto a substrate in accordance with some embodiments of the present disclosure.
Figure 4:
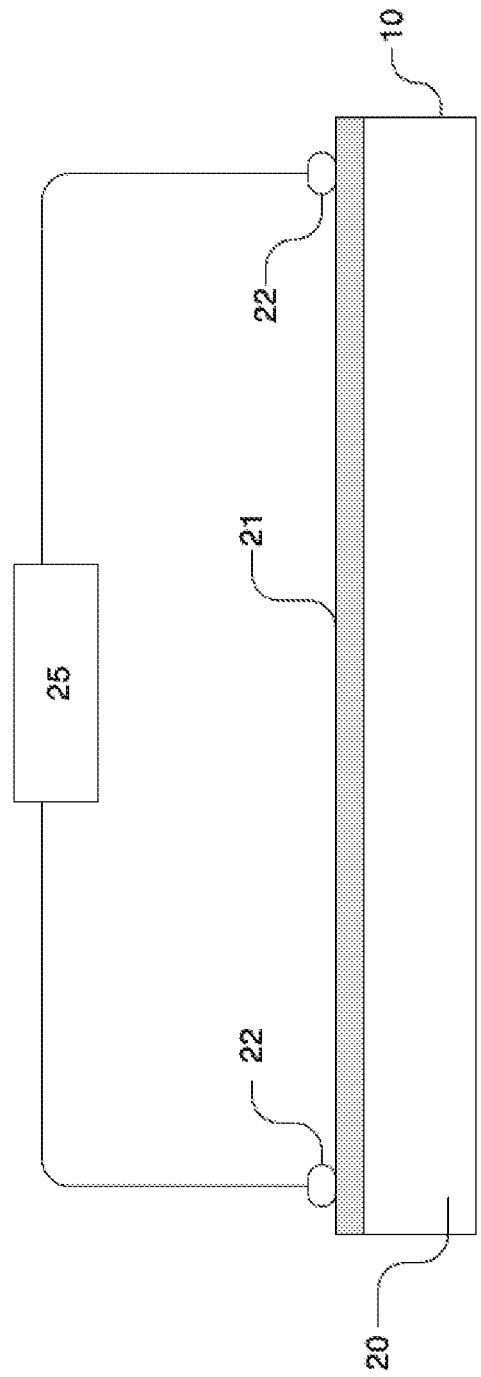
FIG. 4 illustrates an electroconductive material adhered to or deposited onto a substrate, whereby the electroconductive material is in communication with a pair of conductors and a power source in accordance with some embodiments of the present disclosure.
Figure 5:
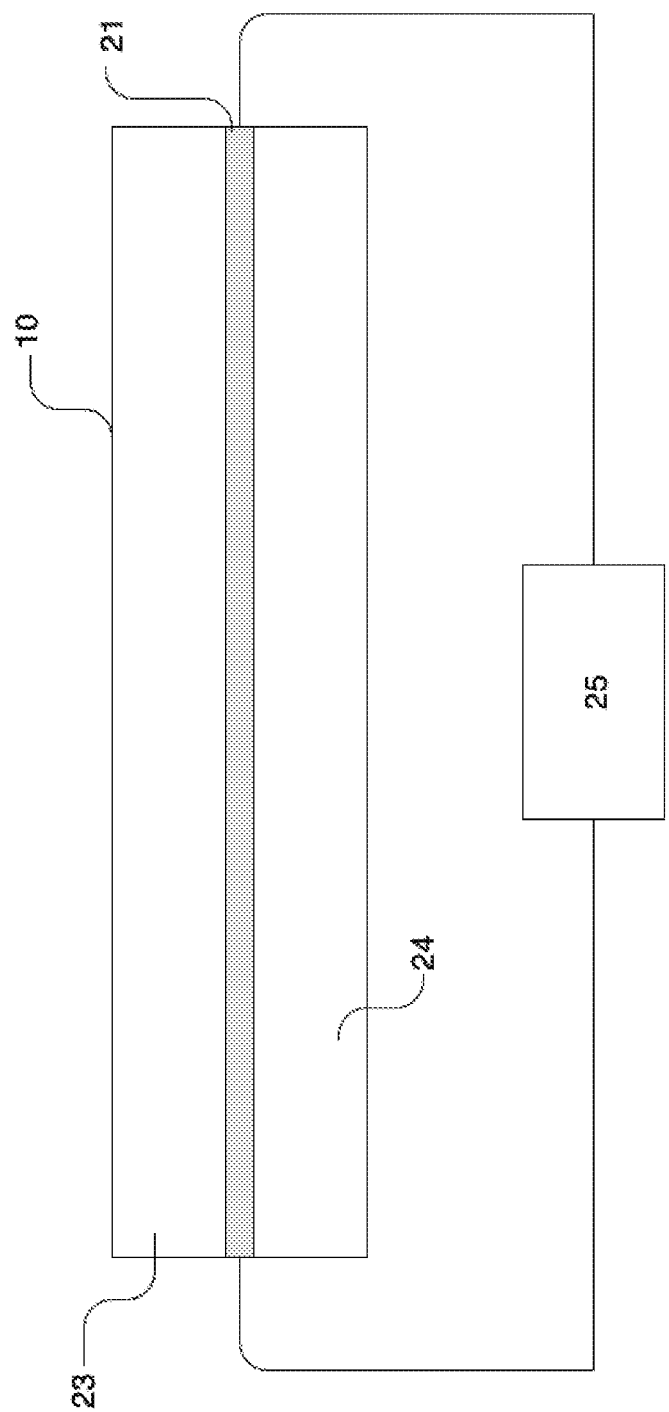
FIG. 5 illustrates an electroconductive material sandwiched between two substrates, whereby the electroconductive material is in communication with a power source in accordance with some embodiments of the present disclosure.

As illustrated in FIGS. 3, 4, and 5, the heated window 10 is itself comprised of multiple components. For example, the heated window 10 may include a substrate 20 and an electroconductive coating or film 21 (see FIGS. 3 and 4). In some embodiments, the electroconductive layer is coated onto or deposited onto the substrate. In some embodiments, the electroconductive layer is a pre-formed layer having an adhesive backing which may be adhered to the substrate. In some embodiments, the heated window 10 may comprise a laminate structure, such as one including first and second substrates 23 and 24, and an electroconductive coating or film 21 sandwiched between the first and second substrates 23 and 24, respectively (see FIG. 5). In some embodiments, the first and second substrates 23 and 24 may be the same or different. For example, substrate 23 may be glass, while substrate 24 may be plastic. In some embodiments, the first and second substrates 23 and 24 are adhered to the electroconductive layer 22 with an adhesive material, such as an optically transparent adhesive material.

In some embodiments, the electroconductive coating or film 21 is disposed onto a substrate 20 having suitable optical, electrical, thermal, and mechanical properties such as, for example, glass, or plastic materials. In some embodiments, the substrate (20, 23, or 24) is selected from soda-lime float glass, aluminosilicate glass, borofloat glass, boroaluminosilicate glass, heat-strengthened glass, tempered glass, or a polymer. Non-limiting examples of polymers include polyimide, polyethylene, napthalate (PEM), polyethylene teraphthallate (PET), aramid or other similar polymer materials. Those skilled in the art will be able to select other polymeric substrates suitable for this purpose and meeting the limitations of the present disclosure. In some embodiments, the substrate has a thickness ranging from between about 0.1 mm to about 3 mm. In other embodiments, the substrate has a thickness ranging from between about 0.1 mm to about 2 mm. In yet other embodiments, the substrate has a thickness ranging from between about 0.1 mm to about 1 mm. In further embodiments, the substrate has a thickness ranging from between about 0.25 mm to about 1 mm.

The electroconductive coating or film 21 may be comprised of any conductive material. Exemplary conductive materials include coatings of indium oxide, indium tin oxide, doped indium oxide, tin oxide, doped tin oxide, zinc oxide, doped zinc oxide, ruthenium oxide, doped ruthenium oxide and the like, as well as all thin metallic coatings that are substantially transparent, comprised of metals including gold, silver, aluminum, nickel alloy, and the like. It is also possible to employ multiple layer coatings, such as those available from Pilkington under the trade name of TEC-Glass®, or those available from PPG Industries under the trade names SUNGATE® 300 and SUNGATE® 500. The electroconductive coating or film 21 may also be a composite conductor prepared by placing highly conductive ceramic and metal wires or conductive layer patterns on one of the faces of the substrate 20 and then over coating this with transparent conductive materials such as indium tin oxide or doped tin oxides. The electroconductive coating or film 21 may be further treated with appropriate anti-reflective or protective oxide or nitride layers.

Alternative conductive materials can also be used. For example, the electroconductive coating or film 21 may be comprised of doped binary compounds such as aluminum-doped zinc oxide (AZO) and indium-doped cadmium oxide. Yet other suitable conductive materials for the electroconductive coating or film 21, include aluminum, gallium or indium-doped zinc oxide (AZO, GZO or IZO), or fluorine tin oxide (FTO).

The electroconductive coating or film 21 may be applied to or deposited on the substrate 20 by any of a wide range of coating processes (e.g., physical vapor deposition (PVD), chemical vapor deposition (CVD), sputtering, etc.) well-known in the art and suitable for the particular substrate and material being deposited. In some embodiments, the electroconductive coating or film 21 has a thickness ranging from between about 1 nm to about 10,000 μm. In other embodiments, the electroconductive coating or film 21 has a thickness ranging from between about 5 nm to about 1,000 μm. In yet other embodiments, the electroconductive coating or film 21 has a thickness ranging from between about 10 nm to about 500 μm. In other embodiments, the electroconductive coating or film 21 has a thickness ranging from between about 10 nm to about 2,500 nm. In yet other embodiments, the electroconductive coating or film 21 has a thickness ranging from between about 10 nm to about 1,000 nm.

In some embodiments, the electroconductive coating or film 21 is substantially uniform in thickness. In other embodiments, the electroconductive coating or film 21 has an intentionally non-uniform thickness such that all areas of the coating or film 21 are uniformly heated regardless of any one area's distance from the conductors 22. In some embodiments, other passive layers used for improving optical properties or providing moisture or scratch resistance may be deposited on top of the electroconductive coating or film 21 or the substrate 20 (depending on orientation).

In some embodiments, the electroconductive coating or film 21 is connected or otherwise communicatively coupled to an electrical power source 25. For example, and as depicted in FIG. 3, a pair of conductors 22 are communicatively coupled to the electroconductive coating or film 21. In some embodiments, the pair of conductors 22 are positioned at opposite ends of the electroconductive coating or film 21. In some embodiments, the pair of conductors 22 are inset from the edges of the heated window 10. In some embodiments, the pair of conductors 22 are positioned or deposited on an inner surface of the heated window 10, i.e. a surface which is enclosed within the sealed housing 2 of the barcode reader 1.

In some embodiments, the pair of conductors 22 are electrical contacts 11 positioned at opposite ends of the heated window 10 (see FIG. 2A). In some embodiments, the electric contacts 11 are conductive pins (e.g. metal pins) which are connected to a circuit board (not depicted) and physically contact a surface of the electroconductive coating or film 21. In some embodiments, the electrical contacts 11 may be fabricated from any of a wide range of electrical conductors, such as, for example, copper, silver, gold, aluminum, zinc, and alloys of these metals. However, the material selected should be compatible with the particular electroconductive coating or film 21 so as to avoid corrosion or other undesired chemical reactions between the electroconductive coating or film 21 and the material of the electrical contacts 11.

In other embodiments, the pair of conductors 22 are bus bars 14 positioned along the periphery of two sides of the heated window 10 (see FIG. 2B). In some embodiments, the bus bars are strips of conductive material deposited or adhered to a surface of the electroconductive coating or film 21, such as strips comprised of copper, silver, gold, aluminum, zinc, etc. In other embodiments, the bus bars 14 are formed from a paste comprising metals or metal alloys. In some embodiments, the bus bars are posited at the opposite ends of the electroconductive coating or film 21 and/or offset from the edges electroconductive coating or film 21.

If the electroconductive coating or film 21 comprises a square configuration, the pair of conductors 22 may be positioned on either pair of opposed ends of the square. Alternatively, if the overall shape of the electroconductive coating or film 21 is rectangular, then it will generally be desirable to place the pair of conductors 22 along the short ends of the rectangular heated window 10, although this is not required. Indeed, whether the pair of conductors 22 are placed on the short ends or the long ends of a rectangular heated window 10 will depend on the overall resistance of the electroconductive coating or film 21, the voltage and current to be provided, as well as on the desired degree of power (heat) dissipation. For example, for a desired power dissipation, the resistance (in ohms per square) of the electroconductive coating or film 21 will need to be greater if the pair of conductors 22 are positioned on the long ends of heated window 10 than if they are placed on the short ends. Conversely, for a given film resistance and applied current, the power dissipation of the electroconductive coating or film 21 will be greater if the pair of conductors 22 are positioned on the long ends of the heated window 10. Of course, the present disclosure is not limited to use with heated windows 10 having rectangular or square configurations, but could be used with other configurations, such as configurations having curved or irregular shapes, by simply shaping the pair of conductors 22 conductors to conform to the particular shape of the electroconductive coating or film 21 or substrate 20.

In some embodiments, the pair of conductors 22 are in communication with a power source 25. In operation, the power supply 25 provides an electrical current to the electroconductive coating or film 21 which becomes heated as a result of the electrical resistance of electroconductive coating or film 21. The construction of the electrical conductors 22 as well as their arrangement in relation to the electroconductive coating or film 21, allows them to deliver an electrical current to the electroconductive coating or film 21 thereby allowing the heated window 10 to dissipate quantities of heat (i.e., power).

In some embodiments, the power supply 25 provides a voltage to the electroconductive coating or film 21 ranging from between about 1V to about 10V. In other embodiments, the power supply 25 provides a voltage of about 5V to the electroconductive coating or film 21. In some embodiments, between about 0.1 Watts to about 2 Watts of power is supplied by the power supply 25 to the electroconductive coating or film 21.

In some embodiments, the power supply 25 provides sufficient power such that the heated window 10 is heated to a temperature ranging from between 30° C. to 60° C. In other embodiments, the power supply 25 provides sufficient power such that the heated window 10 is heated to a temperature ranging from between 30° C. to 50° C. In yet other embodiments, the power supply 25 provides sufficient power such that the heated window 10 is heated to a temperature ranging from between 35° C. to 45° C.

Systems Including a Barcode Reader

The present disclosure also provides a specimen processing system 5, such a staining system, a coverslipping system, etc., that includes one or more barcode readers 1 having a heated window 10 as described herein. Exemplary specimen processing systems are described in U.S. Publication No. 2017/0097288 and in U.S. Pat. No. 8,663,991, the disclosures of which are hereby incorporated by reference herein in their entireties. In some embodiments, the heating of the reagents and fluids applied to a substrate within the specimen processing system 5 creates a build-up of moisture within the specimen processing system 5 and a barcode reader 1 having a heated window is necessary to prevent such moisture from fogging or condensing on the window of the barcode reader 1.

As noted herein, and in some embodiments, the barcode reader 1 having the heated window 10 is used to read a barcode or other indicia present on a label portion of a slide, i.e. the barcode readers disclosed herein having the heated window enables the automatic reading of a barcode affixed to a microscope slide. In some embodiments, the barcode present on a label end of a slide provides an identification of a type of sample disposed on the slide or a type of assay to run. Once a barcode or other indicia is read by the barcode reader having the heated window, data may be transmitted to the staining system or coverslipping system, where it is processed and/or interpreted such that the appropriate fluids or reagents are applied or removed sequentially from a sample and/or applied or removed in the correct order.

In some embodiments, the systems disclosed herein are adapted to automatically prepare biological samples disposed on microscope slides (or other substrates) for pathological analysis. In some embodiments, the preparation of the biological samples is based on information stored within a barcode affixed to a slide. In some embodiments, the systems are configured to perform a series of steps (based on the information read from the barcode affixed to the slide), including baking the biological sample onto the slide by having the instrument apply heat to the biological sufficient to adhere it to the slide; deparaffinizing the biological sample by contacting it with deparaffinizing fluid at a temperature above the melting point of the paraffin, and subsequently rinsing the liquefied paraffin away; staining the biological sample by contacting it with a staining reagent; and/or coverslipping the slide by contacting the stained biological sample on the slide with a pre-glued coverslip and an adhesive activating fluid.

Figure 7:
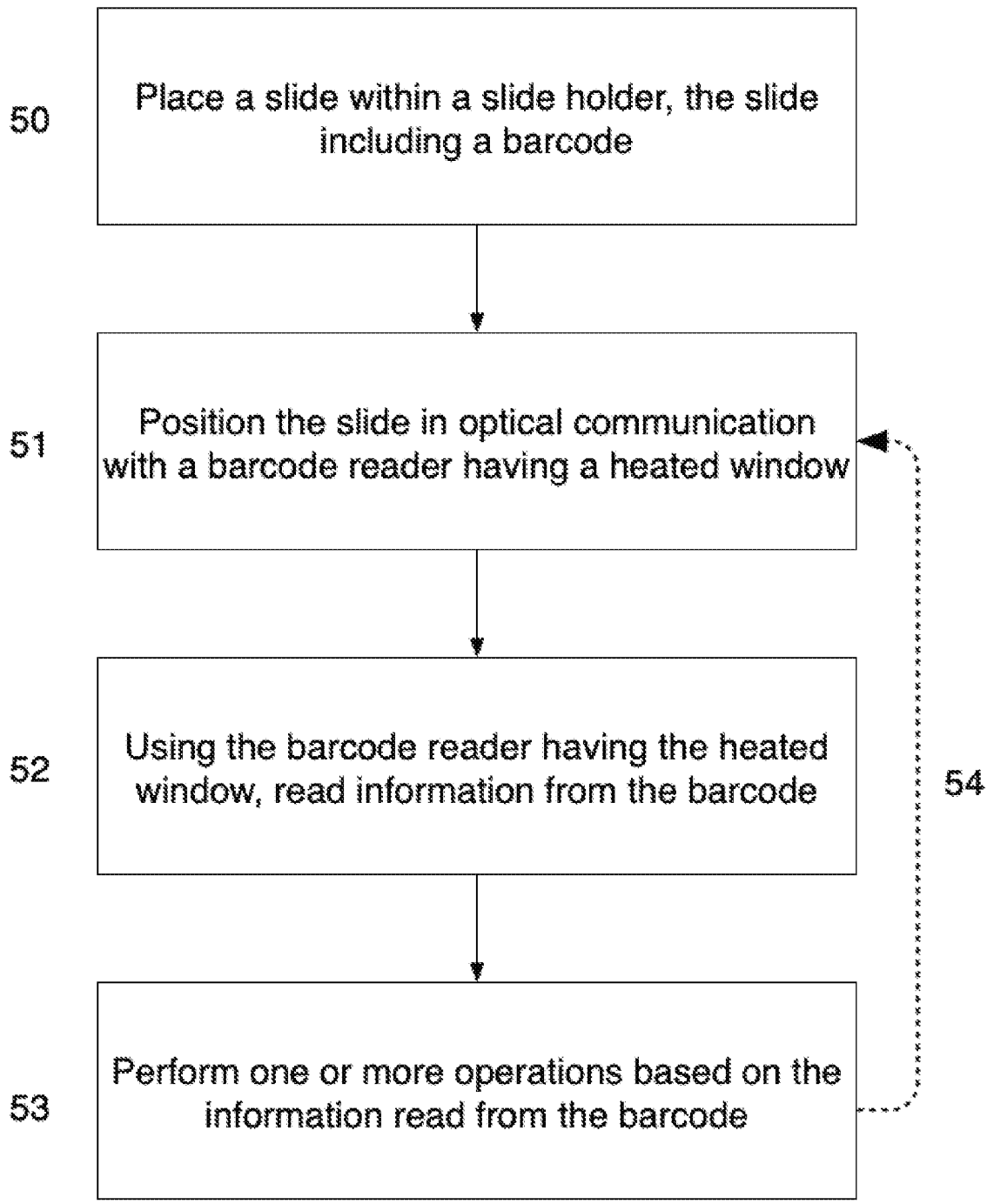
FIG. 7 sets forth a flowchart illustrating the steps of performing one or more slide processing operations based on information read from a label affixed to a slide in accordance with some embodiments of the present disclosure.

With reference to FIG. 7, in some embodiments, a slide having a barcode may be placed within a slide holder (e.g. a slide tray or slide carousel) of a specimen processing system 5 (step 50). In some embodiments, the slide holder is a carousel. In some embodiments, slides are held in a rectangular slide tray in two rows such that their long dimensions are disposed outward from the central, long axis of the tray toward the long edges of the tray. In some embodiments, the specimen processing system 5 includes one or more dispensers, which can move to dispense reagent to slides within each of the row of slides and/or the slide tray can be moved to bring slides into position for reagent dispensing. Alternatively, two or more stationary or moving reagent dispensers can be included in the specimen processing system 5, or one or more manifolds of dispense nozzles can be positioned above the two rows of slides, for example, along the central, long axis of the tray. Nozzles of a reagent dispenser can direct reagent downward and/or upward toward surfaces of slides.

Next, the slide within one of the positions within the slide holder is moved to a position near a barcode reader 1 in accordance with the present disclosure (step 51). Alternatively, the barcode reader 1 may be moved to a position over the slide within the slide holder. In some embodiments, slide carriers can be transferred to a barcode reader having a heated window that reads barcodes affixed to the slides. In some embodiments, a slide may be ejected from the slide carrier towards a barcode reader, and then moved back into the slide carrier.

Subsequently, the barcode reader 1 having the heated window is used by the system to read information from the barcode (step 52). The read information is then used by the system to determine which operations to perform, e.g. which reagents to dispense and in what order they must be dispensed in, or what processing steps need to be applied (e.g. heating, wait times, etc.) (step 53). In some embodiments, barcode information for each slide may be communicated to a controller 6 within specimen processing system 5 for a determination of attributes and/or the sequence of operations that are intended to be performed on the slide for a particular type of assay. Some of these operations may be performed by additional units or modules within specimen processing system. For instance, the slide holders or carriers can be delivered to a processing station which can include, without limitation, a dryer (e.g., a dehydration unit), a heating unit (e.g., a baking module), or other component capable of removing water from the slides, heating specimens (e.g., heating specimens to adhere the specimens to the slides), or the like. In some embodiments, the processing station blows hot air over slides to dry the slides, and if the specimens contain paraffin, the hot air can soften the paraffin to promote adhesion of the specimens to the slides. In some embodiments, the process is repeated for each slide in the slide holder (54). Of course, the process may also be repeated for all slides present in a plurality of slide holders.

By way of example, a first slide having a first barcode may be read by a barcode reader having a heated window, and the data contained within the first barcode may instruct a specimen processing system to consecutively apply hematoxylin, eosin, and an antibody to a first biological sample disposed on the first slide. Likewise, an adjacent second slide having a second barcode may be read by a barcode reader having a heated window, and the data contained with the second barcode may instruct a specimen processing system to consecutively apply hematoxylin and two nucleic acid probes to a second biological sample disposed on the second slide.

Figure 8:
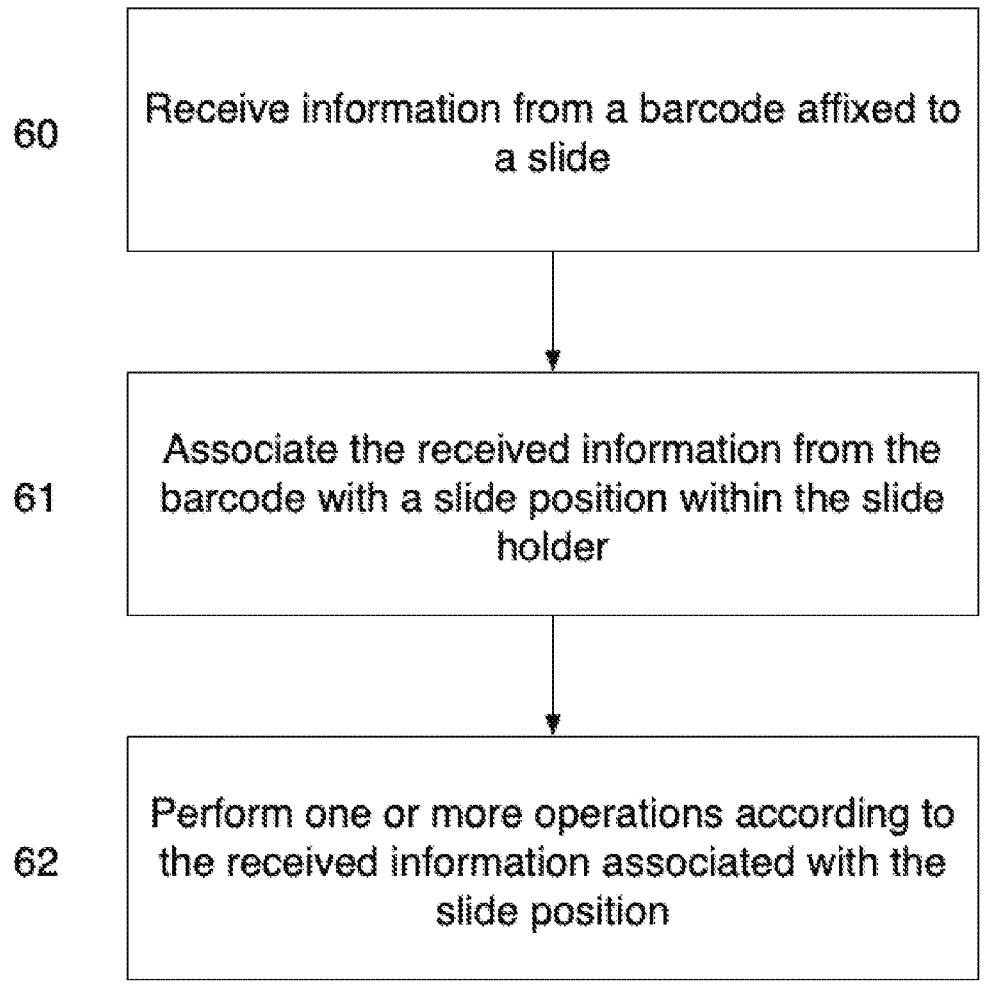
FIG. 8 sets forth a flowchart illustrating the steps of performing one or more slide processing operations based on information read from a label affixed to a slide in accordance with some embodiments of the present disclosure.

Turning to FIG. 8, once the barcode reader 1 having the heated window reads the barcode (step 60), the information is, in some embodiments, associated with a slide position within the slide holder (step 61) (and stored within a memory of controller 6 of specimen processing system 5). When that particular slide position is aligned with a dispense apparatus, etc. within the specimen processing system 5, the specimen processing system 5 will be able to dispense the appropriate reagents and/or fluids, in the appropriate amounts, and in the appropriate order based on the information associated with the slide position (step 62).

In some embodiments, a controller 6 coupled to the specimen processing system 5 can receive slide information from a barcode reader 1 having a heated window that obtains slide information (e.g., a target processing temperature, a target processing temperature range, replenishing rate, etc.) from a barcode of a slide. In some embodiments, the controller can receive additional information such as a total evaporation rate, look-up tables, temperature set points, duty cycles, power settings, environmental information such as ambient temperatures and/or humidity, processing protocols, etc. A processor on the controller or reader may be programmed to read a label or barcode of a slide and communicate with a data server or other similar device in order to retrieve information from a database based on the label. The memory can store different instructions for different processes, including contacting the specimen with a wash, applying a reagent (e.g., a stain) to the specimen, heating and cooling the slide to one or more target temperatures for different processes, etc. The controller may receive the information and execute a plurality of instructions stored in the memory that enable various components of the automated specimen processing system to perform operations that are optimized for the slide based on the label.

In some embodiments, one or more barcode readers having a heated window are incorporated within a specimen processing system 5. In some embodiments, staining of a specimen with a primary stain (e.g. hematoxylin) and a counterstain (e.g. eosin) is accomplished through the use of a specimen processing system 5. In some embodiments, a specimen processing system is an automated apparatus, such as the BENCHMARK XT instrument, the BenchMark Special Stains instrument, the NexES Special Stainer instrument, the SYMPHONY instrument, or the BENCHMARK ULTRA instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 2003/0211630 and 2004/0052685, each of which is incorporated herein by reference in its entirety. Examples of other commercially available specimen processing systems through which hematoxylin and eosin staining compositions may be applied include the VENTANA SYMPHONY (individual slide stainer) and the VENTANA HE 600 (individual slide stainer) series; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH. The barcode readers 1 described herein may be used in conjunction with any of these specimen processing systems. One or more barcode readers 1 having a heated window 10 as described herein may be incorporated into any of these disclosed systems.

In some embodiments, the automated specimen processing system 5 may include a carousel for holding a plurality of substrates, e.g. microscope slides, wherein each substrate includes a biological sample to be stained and a barcode to be read. In some embodiments, the automatic staining apparatus can also include a device for rotating a carousel at predetermined speeds and a mechanism for directing and controlling application of reagents, including the hematoxylin and eosin staining compositions, onto the substrates and samples during rotation of the carousel. In some embodiments, once the slides are loaded into the instrument, test protocols will dictate which fluids are dispensed onto the substrates at specific times, the test protocols, in some embodiments, being determined by information stored in a barcode affixed to a slide and read by a barcode reader having a heated window. At the appropriate time, in some embodiments, a dispenser rack will rotate to align a correct fluid over a substrate and the instrument will dispense a predetermined amount of a fluids onto the substrate. In some embodiments, the instrument will allow the fluid to remain in contact with the biological sample for a predetermined amount of time.

In some embodiments, the automated specimen processing system is used to sequentially or iteratively apply a series of fluids onto a specimen bearing slide, such as needed for a particular assay. For example, the automated specimen processing system may be adapted to dispense hematoxylin and eosin stains to a specimen. In some embodiments, the specimen processing system is configured to apply other fluids both before and after dispensing of the hematoxylin and eosin staining compositions to the biological sample. In the context of H&E staining, the automated specimen processing system may dispense a hematoxylin staining solution to a specimen disposed on a slide. The dispensing of the hematoxylin staining solution facilitates the formation of a first puddle on the slide, which is left in contact with the specimen for a predetermined period of time. Subsequently, this first puddle is at least partially removed to at least partially uncover the specimen. Next, one or more fluids may be applied prior to staining with eosin, whereby each of the one or more fluids applied prior to eosin staining are removed after remaining in contact with the specimen for a predetermined amount of time.

In some embodiments, the automated specimen processing system 5 includes a heating or cooling device (such as a conductive heater or a Peltier device) such that at least one of the biological sample or the fluids applied to the sample are heated to a predetermined temperature and/or for a predetermined amount of time. In some embodiments, the specimen processing system can be configured to provide conductive and/or radiant heating. Conductive heating can be provided via a plate with a resistive heater. One or more lamps can provide radiant heating. The apparatus can controllably increase or decrease the temperature of the specimens. Suitable examples of slide heating devices are described in U.S. Pat. Nos. 7,425,306 and 6,582,962, the disclosures of which are hereby incorporated by reference herein in their entireties. In some embodiments, at least one of the sample or the dispensed fluid is heated to a temperature ranging from between about 30° C. to about 45° C. In other embodiments, the specimen processing system heats at least one of the sample or the dispensed fluid to a temperature ranging from between about 35° C. to about 40° C. In some embodiments, the specimen processing system may heat the sample, the dispensed fluid, or slide for a predetermined period of time, e.g. for between 10 minutes and 40 minutes. Any of the staining reagents and/or fluids dispensed to the specimen or slide may be heated.

In some embodiments, the specimen processing system 5 is configured to apply yet other fluids both before and after dispensing of the hematoxylin and eosin staining compositions to the biological sample. Indeed, the specimen processing system can apply a wide range of substances to the specimen including, without limitation, stains, probes, reagents, rinses, and/or conditioners, or any of the other fluids recited herein. Probes can be an isolated nucleic acid or an isolated synthetic oligonucleotide, attached to a detectable label. Labels can include radioactive isotopes, enzyme substrates, co-factors, ligands, chemiluminescent or fluorescent agents, haptens, and enzymes. In some embodiments, the specimen processing system facilitates performing an immunoassay, for example by incubation with one or more antibodies specific for a particular target bacterium and detected using a label (such as a label on the antibody or via use of a labeled secondary antibody). Exemplary detectable labels include fluorophores, haptens, enzymes, radiolabels, and others known in the art.

In some embodiments, if the specimen is a sample embedded in paraffin, the sample can be deparaffinized with the specimen processing system using appropriate deparaffinizing fluid(s). In some embodiments, and after a waste remover device of a specimen processing system removes any deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

In some embodiments, the system is a workstation that includes a slide tray holding a plurality of slides in a substantially horizontal position and one or more workstations that receive the slide tray and perform one or more slide processing operations on slides in the slide tray. In some embodiments, the barcode reader 1 is positioned above the slide tray or slide carousel such that barcodes affixed to the slide within the slide tray or slide carousel may be read. In some embodiments, the barcode reader 1 is oriented in the direction of a barcode or other symbol on the label end of the slide to be read. The outgoing beam is generated in the barcode reader 1 by a laser diode or the like, is directed through barcode reader's heated window 10 to impinge upon the barcode on affixed to the label end of the slide. The range of the barcode reader 1 may accommodate barcodes positioned from about 1 cm to about 30 cm from the barcode reader 1.

In some embodiments, the workstation can perform a slide processing operation on one or more individual slides in a slide tray, for example, at least two or four slides in a slide tray, or it can simultaneously perform a slide processing operation on all of the slides in a slide tray. In some embodiments, the one or more workstations dispense a reagent to slides in the slide tray without a substantial amount of the reagent that contacts a first slide contacting a second slide, thereby minimizing cross-contamination between slides.

Such workstations can include one or more directional nozzles that dispense the reagent onto the slides, for example, the one or more directional nozzles can include a pair of directional nozzles that dispense the reagent in opposite directions across a surface of a slide. In more particular embodiments, the one or more directional nozzles can further include a directional nozzle that dispenses the reagent towards a bottom surface of a slide. In other particular embodiments, the one or more workstations can simultaneously dispense a reagent (for example, the same reagent) to at least two slides held in a slide tray within a given workstation, or the one or more workstations can simultaneously dispense a reagent (such as the same reagent) to all of the slides held in the slide tray within a given workstation. Additional system components and tray configurations (as well as control systems) are described in U.S. Pat. Nos. 8,663,991, 7,468,161, and 9,528,918, the disclosures of which are hereby incorporated by reference herein in their entireties.

In some embodiments, the workstation may also can include a transporter to move a slide tray into and out of one or more workstations. Another example of a component or workstation that can be part of the disclosed system is a radiant heater, for example, a radiant heater that has a heat profile that provides substantially uniform heating of slides held in a slide tray positioned below the radiant heater. Yet another example of a workstation is a combined de-paraffinizer/stainer. In a particular embodiment, a combined de-paraffinizer/stainer includes a moveable nozzle assembly, wherein the nozzle assembly includes one or more nozzles through which a reagent is dispensed to a slide. The nozzles in the nozzle assembly can be dispense nozzles, forward top surface rinse nozzles that can direct a stream of reagent toward a top surface of a slide (such as at an angle of between about 20 degrees and about 30 degrees relative to the top surface), backward top surface rinse nozzles that can direct a stream of reagent toward a top surface of a slide (such as at an angle of between about 20 degrees and about 50 degrees relative to the top surface), jet drain nozzles, and bottom surface rinse nozzles and combinations thereof. One or more splash guards can also be included on the nozzle assembly as can one or more air brooms or blow-off nozzles.

In another aspect an automated slide processing apparatus 5 is provided that includes a plurality of workstations including a combined de-paraffinizer/stainer, a solvent exchanger, and a coverslipper; a slide tray holding a plurality of slides; a transporter; and one or more barcode readers 1 having a heated window.

At least some embodiments of the present disclosure are directed to a method for processing specimens carried by slides within an automated specimen processing system 5. In some embodiments, the method comprises positioning a barcode reader 1 having a heated window near a slide, such as a slide held in a slide tray. In some embodiments, the barcode reader 1 is adapted to read information contained within a label on one end of a slide. In some embodiments, the method includes moving a slide carrier toward and into a temperature-controlled internal environment of a stainer within the specimen processing system 5. In some embodiments, the barcode reader 1 is incorporated within the temperature-controlled internal environment of the stainer, although because the barcode reader 1 will have its own internal environment due to its sealed housing, the lens within the barcode reader is isolated from the environment of the specimen processing system. In some embodiments, the slide carrier carries a first slide and a second slide, and the first and second slides can carry a first specimen and a second specimen, respectively. The first and second specimens are stained with at least one of a staining reagent and a counterstaining reagent while the first and second slides are within the internal environment and while an average temperature of the internal environment is greater than ambient temperature. In some embodiments, the first and second slides are independently stained based on the information included within the label of each slide. In some embodiments, the slide carrier can be moved out of the internal environment after staining one or both specimens according to information retrieved from the label of each slide.

In some embodiments, an automated specimen processing system 5 comprises a main housing and a stainer. In some embodiments, the stainer includes a stainer housing defining an internal environment of the stainer, one or more heaters configured to internally heat the stainer, and a transporter. In some embodiments, the transporter can be configured to move a slide carrier robotically within the main housing toward the stainer. In one embodiment, the transporter moves the slide carrier between multiple modules in the main housing. As noted herein, the barcode reader 1 comprises a sealed housing including a heated window, the sealed housing defining an interior environment whereby the internal environment within the sealed housing of the barcode reader differences from the internal environment within the stainer.

At least some embodiments are directed to a method for processing specimens in an automated histological staining system. In some embodiments, the method comprises robotically moving a slide carrier into a stainer of the system. In some embodiments, the slide carrier carries slides which respectively carry the specimens, and the specimens are at least partially embedded in paraffin. Liquids are automatically dispensed onto the slides according to a predetermined recipe for at least deparaffinizing, staining, and counterstaining the specimens, based on the information retrieved from a label affixed to the slide. In some embodiments, the slide carrier can be robotically moved out of the stainer after automatically dispensing the liquids. In some embodiments, a total of all liquid dispensed onto the slides after moving the slide carrier into the stainer and before moving the slide carrier out of the stainer has a greater volumetric concentration of polyol than of monohydric alcohol.

EXAMPLE

The goal of testing was to demonstrate whether the barcode reader having the heated window of the present disclosure was effective in mitigating fogging in a high heat and moisture environment, and whether the barcode reader retained its full ability to decode barcodes in these conditions. Testing included a customer-use simulation, adding new slides to the test instruments repeatedly during an in-process slide run producing high heat and humidity conditions within the instrument.

Materials
170 Blank Superfrost Plus slides with the printed Data Matrix labels applied.
ULTRA bulk fluids, including EZ Prep (10×), ULTRA LCS (Predilute), ULTRA Cell Conditioning 1 (CC1), ULTRA Cell Conditioning 2 (CC2), Reaction Buffer (10×), SSC (10×), and UltraView Silver Wash II (all available from Ventana Medical Systems, Tucson, AZ).

Equipment
BenchMark ULTRA (all available from Ventana Medical Systems, Tucson, AZ)

Methods
The new barcode readers were installed in the existing ULTRA system.

Figure 6A:
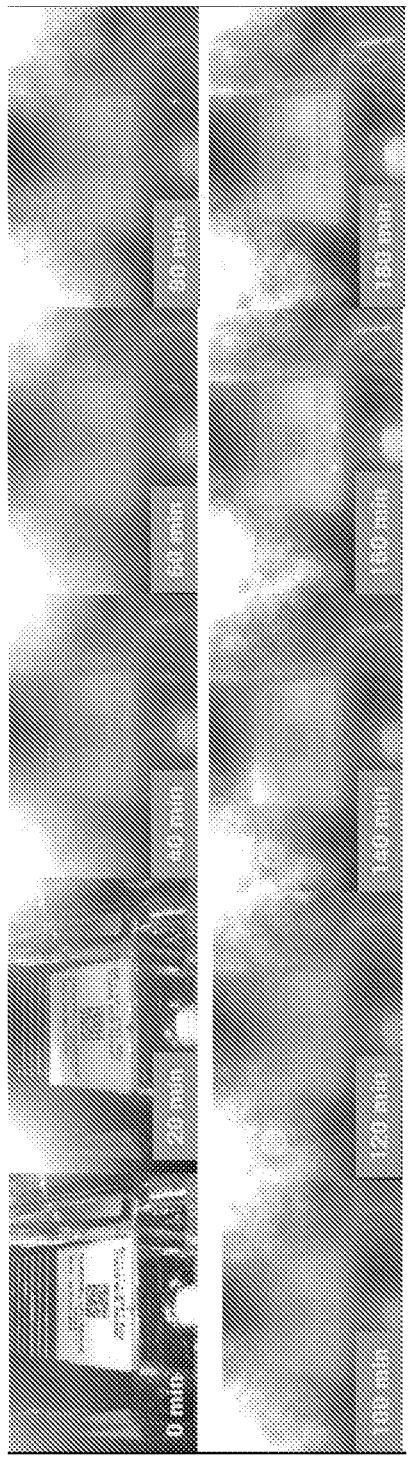
FIG. 6A illustrates the formation of fog or condensate onto the surface of a barcode reader window at ten different time points ranging from 0 minutes to 180 minutes.
Figure 6B:
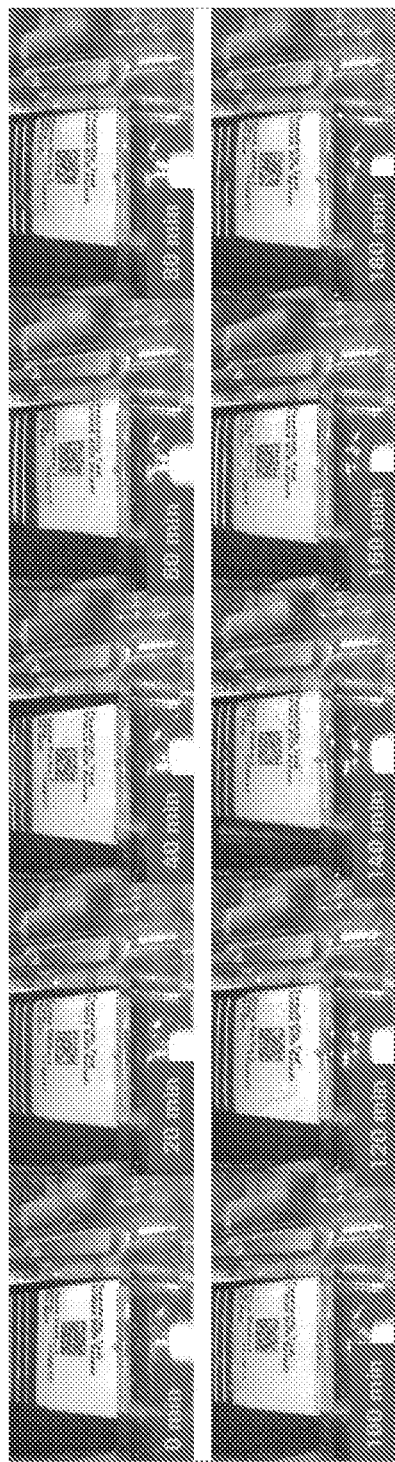
FIG. 6B illustrates that no fog or condensate formed on the surface of a barcode reader heated window at ten different time points ranging from 0 minutes to 180 minutes in accordance with some embodiments of the present disclosure.

Test 1
For Test One, the instrument was loaded with 30 slides labeled for the specified protocol. This protocol was allowed to run to completion (approximately 23.5 hours), producing a hot and humid environment inside the ULTRA instrument. Then, 30 new slides with data matrix labels for the same protocol were loaded into the instrument and a barcode reading test was initiated. All the newly loaded slides were able to be successfully read on the three test instruments. FIG. 6B illustrates images of a barcode reader having a heated window when operated in a high heat and humidity environment over different time periods (namely, every 20 minutes from time 0 through 180-minutes). Notably, none of the heated windows have any fogging or condensation (see FIG. 6B) as compared with FIG. 6A (which shows the results of testing using a standard barcode reader (i.e. without a heated window) under the same testing conditions). FIG. 6A shows, comparatively, that considerable fogging and/or condensation collected on a traditional barcode reader.

Test 2
Test 2 used the same protocol as Test 1, but only 25 slides were loaded into the instrument, leaving five drawers available for periodic new slide insertions. The protocol was allowed to run 10 to 12 hours in order to produce a hot and humid environment inside the instrument. Then, five additional slides labeled for the same protocol were inserted into available drawers. Once these slides were successfully decoded and the new runs had begun, the operator cancelled only the 5 newly inserted slides and removed them from the instrument. The instrument was allowed to run an additional one to two hours and then five more slides were inserted, repeating the exercise. After another wait period to allow the instrument to fully recover the hot and humid environment, the final five slides were inserted and successfully decoded. In each of the three tests with different heated slide barcode readers, all fifteen of the new slides inserted into the hot and humid environment were successfully decoded. The original protocol was allowed to run until completion at which point the barcode scanner was examined and imaged to record its condition.

Results
All slides inserted into a hot and humid instrument environment were successfully decoded and the protocol acceptance criteria were met. The barcode reader having the heated window of the present disclosure was found to successfully decode labels in a worst case, customer use scenario.

Additional Embodiments

In some embodiments, the staining system comprises components in addition to those described herein. Additional embodiments, features, systems, devices, materials, methods, and techniques which may be incorporated into the present systems and methods are described in U.S. Pat. Nos. 8,911,815; 9,498,791; 9,618,430; 7,468,161; and 6,352,861, the disclosures of which are hereby incorporated by reference herein in their entireties. Yet additional components of staining systems are described in U.S. Pat. Nos. 7,303,725, 8,048,373, 9,528,918, and 9,192,935 the disclosures of which are hereby incorporated by reference in their entireties.

In some embodiments, the staining system includes bulk fluid containers (e.g. to hold any of the solutions described herein prior to dispensing or applying to a sample). In some embodiments, slide processing apparatus, in some embodiments, further comprises a plurality of additional staining modules and a controller configured to independently control each of the staining modules.

In some embodiments, the staining system may include a frame supporting a stack of workstations comprising, for example, one or more drying or baking stations or modules, de-waxing or de-paraffinizing station or module, one or more staining stations or modules and a coverslipping station or module arranged in a tower. In some embodiments, a transport and elevator mechanism are provided adjacent to the tower for transporting a slide tray designed to carry a plurality of individual specimen bearing slides from a tray storage station through drying/baking, de-waxing, staining and coverslipping operations.

In some embodiments, a tray storage garage or station comprises a pair of stanchions bearing a plurality of vertically spaced shelves or skids for accommodating slide trays. In some embodiments, the storage station or garage includes a pivotally mounted door providing access to a first shelf position (for clarity, the outside skin or cover to garage has been omitted). A tray drive assembly indicated generally at including a pair of rotatably mounted drive wheels driven by a drive motor and transmission is positioned under the first shelf position for moving a tray into and out of the portal.

In some embodiments, the slide tray comprises a pan or slide tray having a generally rectangular plan, including a bottom wall, opposed side walls and opposed end walls. The slide tray typically is formed by conventional injection molding using synthetic polymers intended for such use, which are well-known in the art.

In some embodiments, the tray includes a specimen slide supporting rack for holding specimen slides in a substantially horizontal position in the same plane. Holding all the slides in the same plane facilitates baking and drying, as will be described below, and also prevents cross-contamination of slides during de-paraffinizing and staining as will be described below. In some embodiments, the rack includes a plurality of slide spring supports that limit the axial, lateral and vertical movement of specimen slides once placed on the slide tray. In some embodiments, the rack is supported above tray bottom at sufficient height to discourage or prevent the formation of films or bubbles forming between the specimen slide bottom and the tray bottom. In some embodiments, the slide spring supports hold the individual specimen slides in position by exerting force on opposing edges of the specimen slides. The floor of the slide tray is sloped towards the middle to facilitate drainage to a central location for evacuation of de-waxing fluids and stains, as will be described in detail hereinafter. In some embodiments, the tray permits the automated handling of a plurality of specimen slides through of the steps of drying/baking, de-paraffinizing, staining and coverslipping. In some embodiments, the tray includes splash rails and is arranged to accommodate 16 specimen slides arranged in a generally horizontal grid two slides wide and eight slides tall.

The staining module can include at least one heating element positioned to conductively heat the first sidewall, the second sidewall, or both. The slide holder can be used to heat the slide, specimen, and/or liquid while the band of liquid is manipulated across the specimen.

The controller, in some embodiments, includes one or more memories and a programmable processor. The memory stores a first sequence of program instructions and a second sequence of program instructions. The programmable processor is configured to execute the first sequence of program instructions in order to process a specimen on the slide with a first liquid and configured to execute the second sequence of program instructions to process the specimen with a second liquid that is different from the first liquid. In some embodiments, the programmable processor is configured to execute the first sequence of program instructions in order to heat the slide and the controller is configured to execute the second sequence of program instructions in order to heat the slide to a second temperature, the second temperature is different from the first temperature.

The controller, in some embodiments, is configured to execute a first sequence of program instructions to command the dispensing device to deliver a first liquid to the slide at a first rate. The controller is further configured to execute a second sequence of program instructions to command the dispensing device to deliver a second liquid to the slide at a second rate that is different from the first rate.

At least some of the embodiments of the present disclosure relate to computer systems or computers integrated into a systems' controller or control system. A digital pathology system may comprise an imaging apparatus (e.g. an apparatus having means for scanning a specimen-bearing microscope slide) and a computer, whereby the imaging apparatus and computer may be communicatively coupled together (e.g. directly, or indirectly over a network). The computer system can include a desktop computer, a laptop computer, a tablet, or the like, digital electronic circuitry, firmware, hardware, memory, a computer storage medium, a computer program or set of instructions (e.g. where the program is stored within the memory or storage medium), one or more processors (including a programmed processor), and any other hardware, software, or firmware modules or combinations thereof (such as described further herein). For example, the computing system may comprise a computer with a display device and an enclosure.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Any of the modules described herein may include logic that is executed by the processor (s). "Logic," as used herein, refers to any information having the form of instruction signals and/or data that may be applied to affect the operation of a processor. Software is an example of logic.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

The imaging system or apparatus may be a multispectral imaging (MSI) system or a fluorescent microscopy system. The imaging system used here is an MSI. MSI, generally, equips the analysis of pathology specimens with computerized microscope-based imaging systems by providing access to spectral distribution of an image at a pixel level. While there exists a variety of multispectral imaging systems, an operational aspect that is common to all of these systems is a capability to form a multispectral image. A multispectral image is one that captures image data at specific wavelengths or at specific spectral bandwidths across the electromagnetic spectrum. These wavelengths may be singled out by optical filters or by the use of other instruments capable of selecting a pre-determined spectral component including electromagnetic radiation at wavelengths beyond the range of visible light range, such as, for example, infrared (IR).

An MSI system may include an optical imaging system, a portion of which contains a spectrally-selective system that is tunable to define a pre-determined number N of discrete optical bands. The optical system may be adapted to image a biological sample, illuminated in transmission with a broadband light source onto an optical detector. The optical imaging system, which in one embodiment may include a magnifying system such as, for example, a microscope, has a single optical axis generally spatially aligned with a single optical output of the optical system. The system forms a sequence of images of the biological as the spectrally selective system is being adjusted or tuned (for example with a computer processor) such as to assure that images are acquired in different discrete spectral bands. The apparatus may additionally contain a display in which appears at least one visually perceivable image of the biological sample from the sequence of acquired images. The spectrally-selective system may include an optically-dispersive element such as a diffractive grating, a collection of optical filters such as thin-film interference filters or any other system adapted to select, in response to either a user input or a command of the pre-programmed processor, a particular pass-band from the spectrum of light transmitted from the light source through the sample towards the detector.

An alternative implementation, a spectrally selective system defines several optical outputs corresponding to N discrete spectral bands. This type of system intakes the transmitted light output from the optical system and spatially redirects at least a portion of this light output along N spatially different optical paths in such a way as to image the sample in an identified spectral band onto a detector system along an optical path corresponding to this identified spectral band.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. An automated specimen processing system, comprising:
   a slide holder comprising one or more slides, wherein each slide of the one or more slides includes identifying indicia;
   at least one barcode reader having a sealed housing including a heated window; and
   a dispenser configured to independently deliver one or more fluids and/or reagents to each slide of the one or more slides based on the identifying indicia present on each slide of the one or more slides; and
   an enclosure, wherein at least the at least one barcode reader is positioned within the enclosure, and wherein a first environment within the sealed housing of the at least one barcode reader has a first temperature and/or a first humidity which is less than a second temperature and/or humidity of a second environment within the enclosure but outside of the at least one barcode reader.

2. The automated specimen processing system of claim 1, wherein the automated specimen processing system further comprises a control module in communication with the at least one barcode reader.

3. The automated specimen processing system of claim 2, wherein the control module is configured to receive information from the at least one barcode reader and command the dispenser to dispense one or more fluids and/or reagents based on the information received from the at least one barcode reader.

4. The automated specimen processing system of claim 1, wherein the heated window comprises an electroconductive layer, wherein the electroconductive layer is in communication with a power source.

5. The automated specimen processing system of claim 4, wherein the power source supplies between about 1V and about 10V to the electroconductive layer.

6. The automated specimen processing system of claim 4, wherein the electroconductive layer is comprised of indium tin oxide.

7. The automated specimen processing system of claim 1, wherein a temperature of the heated window ranges from between about 30° C. and about 60° C.

8. The automated specimen processing system of claim 1, wherein a temperature of the heated window ranges from between about 35° C. and about 50° C.

9. An apparatus for automatically treating biological specimens disposed on a slide, comprising:
   at least one slide tray for holding a one or more of slides, wherein each slide of the one or more slides is held in a substantially horizontal position;
   at least one barcode reader comprising a sealed housing having a heated window;
   one or more workstations that receive the slide tray; and
   a transporter that moves the slide tray into and out of the one or more workstations;
   wherein the apparatus further comprises an enclosure, wherein the at least one barcode reader is positioned within the enclosure, wherein an environment inside the enclosure has a greater temperature and/or humidity than an environment inside the sealed housing of the at least one barcode reader.

10. The apparatus of claim 9, further comprising a fluidics module in fluid communication with the one or more workstations that supplies one or more reagents to the one or more workstations.

11. The apparatus of claim 9, further comprising a pneumatics module in fluid communication with the one or more workstations and the fluidics module; wherein the pneumatics module supplies vacuum and/or pressurized gas to the one or more workstations and the fluidics module.

12. The apparatus of claim 11, further comprising a control module in communication with the at least one barcode reader, the transporter, the one or more workstations, the fluidics module and/or the pneumatics module, wherein the control module coordinates function of components of the apparatus during treatment of the biological specimens based on information received from the at least one barcode reader.

13. The apparatus of claim 9, wherein at least one of the one or more workstations that receive the slide tray and perform the one or more slide processing operation comprises a moveable nozzle assembly.

14. The apparatus of claim 9, wherein a temperature of the heated window ranges from between about 30° C. and about 60° C.

15. The apparatus of claim 9, wherein a temperature of the heated window ranges from between about 35° C. and about 50° C.

16. An apparatus for automatically treating biological specimens, comprising:
- at least one slide tray for holding one or more slides, wherein each slide of the one or more slides are held in a substantially horizontal position;
- at least one barcode reader comprising: a sealed housing including an optically transparent window, wherein the optically transparent window comprises a substrate and an electroconductive layer disposed on a surface of the substrate; a pair of conductors, wherein each conductor of the pair of conductors is in contact with the electroconductive layer; and a power source in communication with the pair of conductors;
- one or more workstations that receive the slide tray; and
- a transporter that moves the slide tray into and out of the one or more workstations,
- wherein the apparatus further comprises an enclosure, wherein the at least one barcode reader is positioned within the enclosure, wherein an environment inside the enclosure has a greater temperature and/or humidity than an environment inside the sealing housing of the at least one barcode reader.

17. The apparatus of claim 16, wherein the pair of conductors are first and second bus bars.

18. The apparatus of claim 16, wherein the power source supplies between about 1V to about 10V to the electroconductive layer.

19. The apparatus of claim 16, wherein the one or more workstations include one or more directional nozzles configured to dispense one or more fluids and/or reagents to the one or more slides.

20. The apparatus of claim 16, further comprising a heater.

21. The apparatus of claim 16, further comprising a coverslipper.

22. The apparatus of claim 16, further comprising a solvent exchanger.

\* \* \* \* \*